(12) United States Patent
Wang et al.

(10) Patent No.: US 9,949,880 B2
(45) Date of Patent: Apr. 24, 2018

(54) ABSORBENT ARTICLE WITH EMBEDDED LATERAL TOPSHEETS

(71) Applicant: The Procter & Gamble Company, Cincinnati, OH (US)

(72) Inventors: Fancheng Wang, Beijing (CN); Tianjun Niu, Guangzhou (CN); Wolfgang Werner Hans Domeier, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/091,836

(22) Filed: Nov. 27, 2013

(65) Prior Publication Data
US 2015/0148765 A1    May 28, 2015

(51) Int. Cl.
*A61F 13/475* (2006.01)
*A61F 13/513* (2006.01)

(52) U.S. Cl.
CPC .... *A61F 13/51305* (2013.01); *A61F 13/4751* (2013.01); *A61F 2013/51383* (2013.01)

(58) Field of Classification Search
CPC ............. A61F 13/4751; A61F 13/4755; A61F 13/4756; A61F 13/4757; A61F 13/4942; A61F 13/49446; A61F 13/51104; A61F 13/51108; A61F 13/51305
USPC ................................ 604/378–381, 385.101
See application file for complete search history.

(56) References Cited

U.S. PATENT DOCUMENTS

| | | | |
|---|---|---|---|
| 3,575,174 A * | 4/1971 | Mogor | 604/385.01 |
| 5,431,643 A | 7/1995 | Ouellette et al. | |
| 5,533,991 A | 7/1996 | Kirby et al. | |
| 6,117,523 A * | 9/2000 | Sugahara | 428/134 |
| 6,365,795 B1 | 4/2002 | Suekane et al. | |
| 6,586,653 B2 | 7/2003 | Graeme, III et al. | |
| 6,717,028 B1 * | 4/2004 | Oberstadt | 604/365 |
| 6,984,770 B2 | 1/2006 | Graeme, III et al. | |
| 8,251,965 B2 | 8/2012 | Costea et al. | |

(Continued)

FOREIGN PATENT DOCUMENTS

| | | |
|---|---|---|
| CN | 2012-19950 Y | 4/2009 |
| JP | 2001-037810 | 2/2001 |

(Continued)

OTHER PUBLICATIONS

PCT International Search Report, dated Sep. 12, 2013 (13 pages).

*Primary Examiner* — Kathryn E Ditmer
(74) *Attorney, Agent, or Firm* — George H. Leal; Andrew John Mueller

(57) ABSTRACT

The present invention relates to an absorbent article having a body-facing surface and a transverse centerline, comprising; a hydrophilic topsheet, a backsheet joined to the topsheet, and an absorbent core disposed between the topsheet and the backsheet, and a lateral topsheet on each longitudinal side of the body-facing surface of the absorbent article so that at least a part thereof covers the topsheet where the topsheet covers the absorbent core, wherein the lateral topsheet comprises an embedded zone along the longitudinal direction of the absorbent article comprising a plurality of compressed areas where the lateral topsheet and the topsheet are jointly compressed so that the lateral topsheet is embedded into the topsheet, and wherein the lateral topsheet in the compressed areas is one layer.

12 Claims, 3 Drawing Sheets

(56) References Cited

U.S. PATENT DOCUMENTS

| | | | |
|---|---|---|---|
| 2001/0039406 A1* | 11/2001 | Hamajima et al. | 604/367 |
| 2003/0109839 A1 | 6/2003 | Costea et al. | |
| 2003/0114809 A1 | 6/2003 | Gagliardi et al. | |
| 2003/0204178 A1 | 10/2003 | Febo et al. | |
| 2006/0229579 A1* | 10/2006 | Wahlstrom et al. | 604/366 |
| 2008/0249494 A1* | 10/2008 | Digiacomantonio et al. | 604/378 |
| 2010/0168707 A1* | 7/2010 | Nishikawa et al. | 604/383 |
| 2011/0046592 A1 | 2/2011 | Nishikawa et al. | |

FOREIGN PATENT DOCUMENTS

| | | |
|---|---|---|
| JP | 2009-011685 | 1/2009 |
| JP | 2009-11686 | 1/2009 |
| JP | 2009011686 A * | 1/2009 |
| WO | WO 2005-084596 A1 | 9/2005 |
| WO | WO 2008-146702 A1 | 12/2008 |

* cited by examiner

ABSORBENT ARTICLE WITH EMBEDDED LATERAL TOPSHEETS

FIELD OF THE INVENTION

The invention relates to absorbent articles for external use. More specifically the invention relates to absorbent articles having an embedded zone on each of lateral sides of a body-facing surface of the article.

BACKGROUND OF THE INVENTION

Absorbent articles such as sanitary napkins are used by women during their menstrual periods to receive and contain blood discharges from the vagina. In addition to collecting body fluids like menses, these articles are also expected to protect the wearer's undergarment from body fluid contamination.

As absorbent articles are normally placed between the wearer's crotch and her undergarment, they can be easily deformed by motion of the wearer which often causes leakage of body fluid toward laterally opposed edges of the absorbent article. One approach to resolve a side leakage concern is to provide an absorbent article with side sheets, especially hydrophobic side sheets, in the side edges of an absorbent body of the absorbent article. The side sheets are bonded with a topsheet and/or a backsheet by a bonding method such as heat-sealing and heat-embossing, etc. Japanese patent laid-open No. 2009-11686 discloses absorbent articles having hydrophobic side sheets with folded inner ends which may be spaced apart from a topsheet. These articles, by having side sheets with folded inner ends which may be spaced apart from a topsheet, are intended to prevent the fluid like menstrual blood from bleeding on the side sheets separated from a topsheet when a large amount of fluid spreads out to the width of the topsheet the central portion of the absorbent articles. Absorbent articles disclosed in the reference mentioned above would effectively prevent body fluids reached on a topsheet of the absorbent article from leaking laterally, however, there is still unsolved problem that when the body fluid is placed on top of the side sheets, the hydrophobic side sheets folded and spaced from a topsheet cannot prevent the fluid effectively go into the product, thus leading to fluid leakage.

There is therefore a need for an absorbent article providing more effective side leakage prevention.

SUMMARY OF THE INVENTION

The present invention provides an absorbent article comprising a hydrophilic topsheet, a backsheet joined to the topsheet, an absorbent core disposed between the topsheet and the backsheet, and a lateral topsheet on each longitudinal side of the body-facing surface of the absorbent article so that at least a part thereof covers the topsheet where the topsheet covers the absorbent core, wherein the lateral topsheet comprises an embedded zone along the longitudinal direction of the absorbent article comprising a plurality of compressed areas where the lateral topsheet and the topsheet are jointly compressed so that the lateral topsheet is embedded into the topsheet, and wherein the lateral topsheet in the compressed areas is one layer.

The present invention also provides an absorbent article comprising a hydrophilic topsheet, a backsheet, an absorbent core disposed between the topsheet and the backsheet, and a lateral topsheet on each longitudinal side of the body-facing surface of the absorbent article so that at least a part thereof covers the topsheet where the topsheet covers the absorbent core, wherein the lateral topsheet comprises an embedded zone along the longitudinal direction of the absorbent article comprising a plurality of compressed areas where the lateral topsheet, the topsheet, and at least a part of the absorbent core are jointly compressed so that the lateral topsheet are embedded into the topsheet, and wherein the lateral topsheet in the compressed areas is one layer.

These and other features, aspects, and advantages of the present invention will become evident to those skilled in the art from a reading of the present disclosure.

BRIEF DESCRIPTION OF THE DRAWINGS

FIG. 2 (*b*) is a mimetic diagram of a cross section view of modified example of embossing depth in the article according to the present invention.

DETAILED DESCRIPTION OF THE INVENTION

All ranges are inclusive and combinable. The number of significant digits conveys neither limitations on the indicated amounts nor on the accuracy of the measurements.

The term "absorbent articles" as used herein, include disposable diapers, sanitary napkins, panty liners, incontinence pads, interlabial pads, breast-milk pads, sweat sheets, animal-use excreta handling articles, animal-use diapers, and the like.

The term "body-facing surface" refers to the side of the absorbent article facing the body of the user when in use. The term "garment facing surface" refers to the opposite surface of the article.

The terms "body fluid(s)," or "the fluid", used herein, include, but are not limited to menses, vaginal discharges, blood, sweat, and combinations of these substances.

The term "longitudinal centerline", as used herein, refers to the imaginary line centered between the longitudinal side edges of the absorbent article and which is generally aligned with the vertical plane which bisects a standing wearer into left and right body halves and is represented by the line C on the drawings. The length L of the article indicates the longest length of the article in the longitudinal direction.

The term "transverse centerline", as used herein, refers to the imaginary line T centered between the transversal side edges of the absorbent article and which is perpendicular to the longitudinal centerline.

The term "inner side", as used herein, means a central portion in the width direction of the absorbent article 10. Similarly, "outer side" means a side edge side of the absorbent article.

Figure 1:
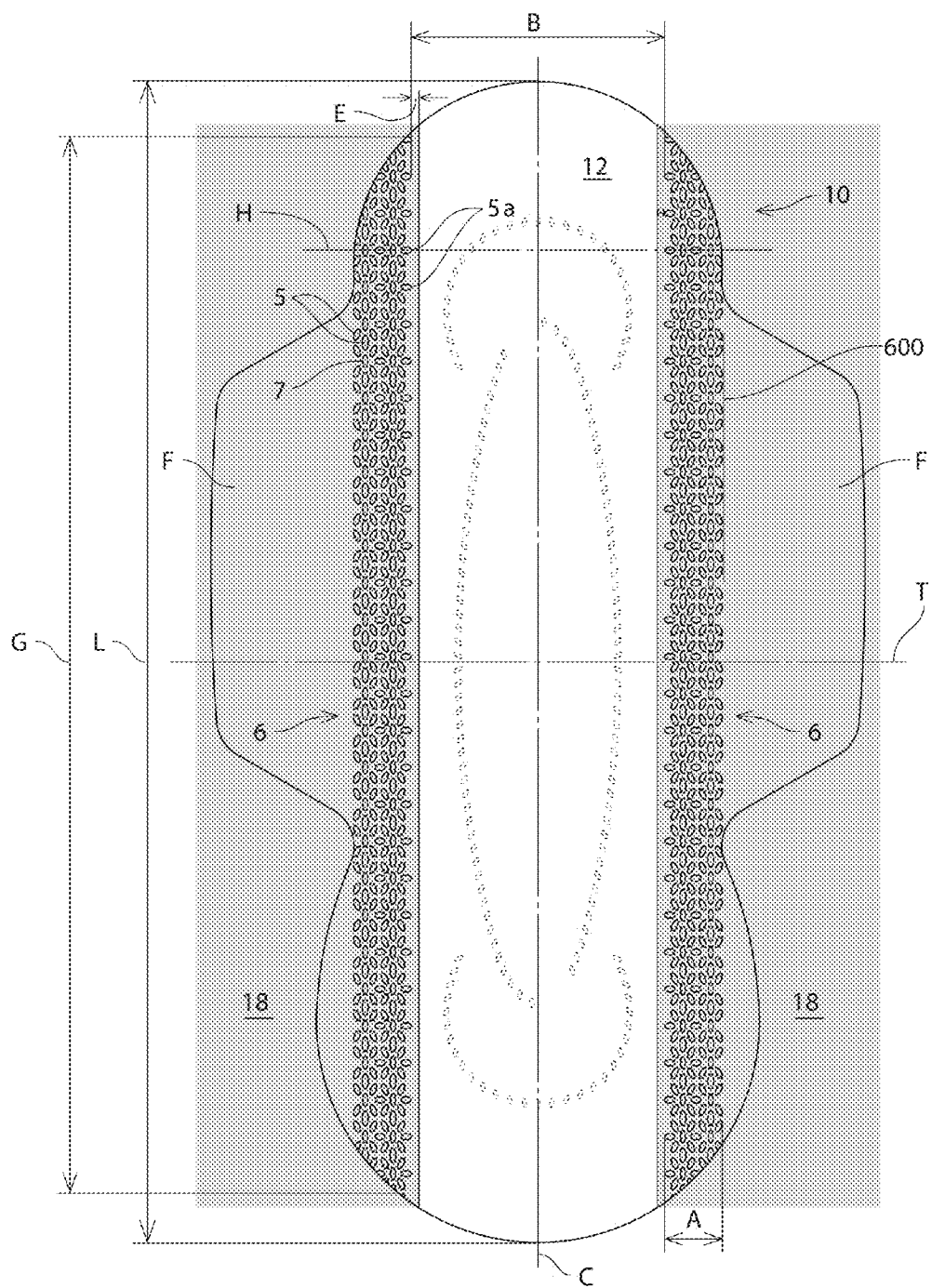
FIG. 1 is a top view of an exemplary absorbent article according to the present invention.
Figure 2:
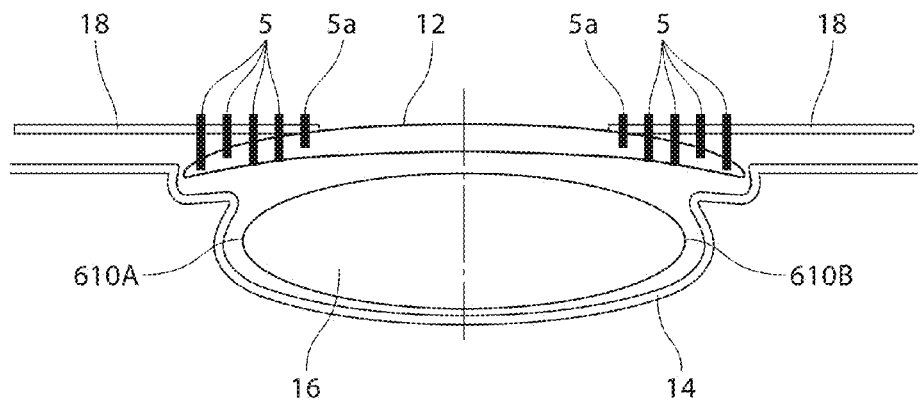
FIG. 2 (*a*) is a mimetic diagram of a cross section view taken along line H of the article according to FIG. 1.
Figure 2:
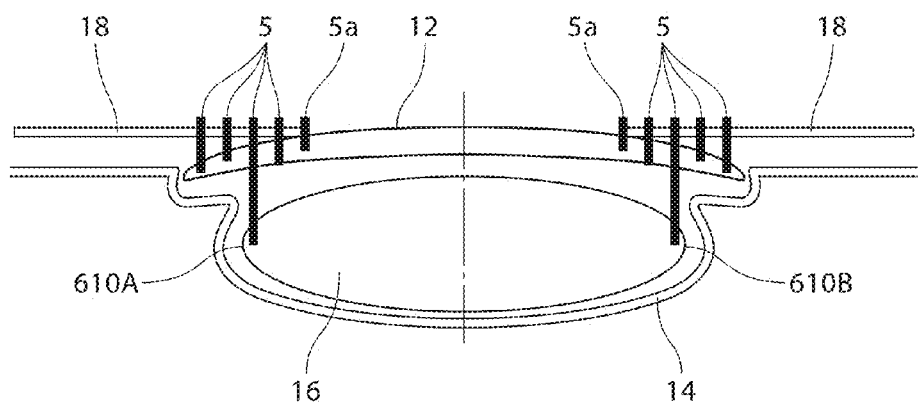
Figure 3:
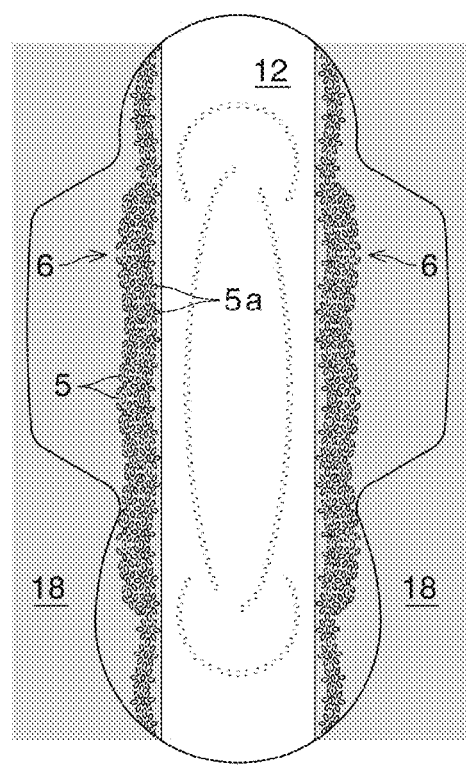
FIG. 3 is a top view of an exemplary absorbent article according to the present invention.
Figure 4:
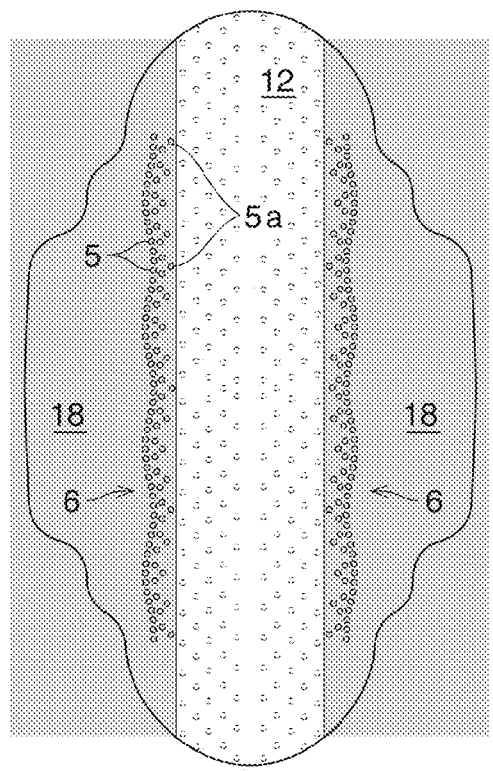
FIG. 4 is a top view of an exemplary absorbent article according to the present invention.

FIG. 1 shows the body-facing surface of an exemplary absorbent article 10 according to the present invention. The body-facing surface of the absorbent article 10 shows the hydrophilic topsheet 12, the lateral topsheets 18 having an embedded zone 6 comprising compressed areas 5, 5*a* on each lateral topsheet. FIG. 2(*a*) and FIG. 2(*b*) are mimetic diagrams of cross section view of exemplary absorbent articles according to the present invention, showing the hydrophilic topsheet 12, the lateral topsheets 18, the compressed areas 5, 5a, and the absorbent core 16 and the backsheet 14. FIGS. 3 and 4 show the body-facing surfaces of exemplary absorbent articles according to the present invention. It should be noted that the present invention is not limited to the configurations shown on FIGS. 1-4.

Absorbent Article 10

As shown in FIG. 1, FIGS. 2 (*a*) and (*b*), the absorbent articles of the present invention normally comprise the topsheet 12, a backsheet 14, an absorbent core 16 disposed between the topsheet 12 and backsheet 14, and a lateral topsheets 18 having an embedded zone 6 on each longitudinal side of the absorbent article atop the topsheet 12. The topsheet 12 and the lateral topsheets 18 partially, or completely, form the body-facing surface of the article, whilst the backsheet jointed to the topsheet and/or lateral topsheets forms the garment-facing surface. The topsheet 12 covers the entire upper side of the absorbent core 16, and slightly extends laterally outward from the longitudinal sides of the absorbent core 16. It also extends outwards from the front and the back ends of the absorbent core 16, and joins with a backsheet 14 in the extensions. The lateral topsheets 18 are deposited to cover both side portions of absorbent core 16 so that the lateral topsheets cover a part of the topsheet 12 and extends outwards to join the backsheet 14 to cover sides of the absorbent article.

Further additional elements to improve the performance of the articles may also be used and are represented, such as a secondary topsheet, and/or a secondary backsheet. The article may also comprise a release paper.

Hydrophilic Topsheet 12

The absorbent article of the present invention comprises a hydrophilic nonwoven topsheet 12. A hydrophilic nonwoven sheet 12 can catch body fluids and allow the fluid penetration inside the absorbent article quickly.

The term "hydrophilic", as used herein, describes fibers, surfaces of fibers, or surfaces of material which are wettable by aqueous fluids (e.g., aqueous body fluids) deposited on these fibers. Hydrophilicity and wettability are typically defined in terms of contact angel and the strike-through time of the fluids, for example through a nonwoven fabric. This is discussed in detail in the American Chemical Society Publication entitled "Contact Angle, Wettability and Adhesion", edited by Robert F. Could (Copyright 1964). A fiber or surface of a fiber is said to be wetted by a fluid (1 . . . , hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90°, and the fluid does not spread spontaneously across the surface of the fiber.

The term "nonwoven", as used herein, is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wetmilling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electro spinning, and carding. The basis weight of nonwoven fabrics is usually expressed in grams per square meter gsm).

Hydrophilic nonwoven can be made of hydrophilic fibers treated with a treatment agent, such as a hydrophilic agent, rendering the fibers hydrophilic. Alternatively, or in addition, hydrophilic nonwoven can be prepared by treating nonwoven (after nonwoven formation) with a hydrophilic agent. Such hydrophilic agents may for example include or be a surfactant. Treatment of nonwoven with surfactant can be accomplished by any of the common techniques well known to those skilled in the art. For example, the surfactant can be applied to nonwoven topsheet by spray, by padding, or by the use of transfer rolls.

The topsheet is a layer of the article that contacts the body of the wearer and receives bodily discharges. The topsheet is liquid pervious and may be flexible and non-irritating to the skin. The term "liquid pervious" as used herein refers to components that allow liquids to pass therethrough without significantly retarding or obstructing the transmission of such liquids therethrough. As used herein the term "flexible" refers to materials which are compliant and readily conform to the shape of the body or respond by easily deforming in the presence of external forces. Components are considered absorbent if such components not only transmit such liquids, but also can retain a portion of the liquids deposited on such components. Any conventional hydrophilic nonwoven topsheet materials may be used within the invention.

The topsheet may have a plurality of apertures to permit liquids deposited thereon to pass through to the core. An apertured polyolefinic film topsheet having about 5 to about 50 percent open area, typically about 25 percent open area, and a thickness of about 0.01 to about 0.03 millimeters prior to aperturing and about 0.42 to about 0.51 millimeters after aperturing is usual.

The topsheet may have a basis weight of from about 10 gsm to about 100 gsm, preferably from about 30 gsm to about 80 gsm to allow fast fluid penetration inside of an absorbent article.

Absorbent Core 16

The article of the invention comprises an absorbent core 16 disposed between the topsheet 12 and the backsheet 14. As used herein, the term "absorbent core" refers to a material or combination of materials suitable for absorbing, distributing, and storing aqueous fluids such as urine, blood, menses, and other body exudates.

The size and shape of the absorbent core can be altered to meet absorbent capacity requirements, and to provide comfort to the wearer. As with the other elements of the articles of the invention, there are no particular requirements for the absorbent core and any standard liquid-absorbent material known in the art for use in absorbent articles will normally be suitable.

Non-limiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The core, as the article itself, may be generally planar, i.e. does not have a significant variation in thickness.

Typically the absorbent core is rectangularly shaped, for ease of manufacturing. However, the core may be differently shaped, for example there is frequently a wearer preference for an absorbent core which is narrower at the center than at the ends, to comfortably accommodate the legs, and obviate or minimize occurrences of bunching or wadding of the core. Oval shaped core have also been proposed (e.g. WO2005/084596). Further generic and specific information regarding absorbent cores can be found for example in WO0207662A1 and WO09119471.

Backsheet 14

The article of the invention comprises backsheet 14. The backsheet 14 may be any flexible, liquid, resistant, and liquid impervious material. The backsheet prevents discharges collected by and contained in the sanitary napkin, and particularly discharges absorbed by the core, from escaping the sanitary napkin and soiling the clothing and bedding of the wearer. Preferably the backsheet is not noisy, to provide discretion for the wearer. In some executions, a secondary backsheet (discussed below) may be placed intermediate the core and the backsheet to second the backsheet, for example to provide liquid imperviousness.

Any conventional backsheet materials may be used within the invention, such as polyolefinic films. The backsheet may be impervious to malodorous gases generated by absorbed bodily discharges, so that the malodors do not escape. The backsheet may or may not be breathable. A low density polyethylene backsheet about 0.01 to about 0.08 millimeters in thickness, preferably about 0.05 millimeters in thickness, is usual. A polyethylene film, such as is sold by the Tredegar Corporation of Terre Haute, Ind., under model X-813 may be used. Further, the backsheet may be made of a soft cloth like material which is hydrophobic relative to the topsheet, e.g. a polyester or polyolefinic fiber backsheet.

The topsheet and the backsheet are preferentially peripherally joined using known techniques, either entirely so that the entire perimeter of the sanitary article is circumscribed by such joinder or are partially peripherally joined at the perimeter. The term "joined" refers to the condition where a first component is affixed, or connected, to a second component either directly; or indirectly, where the first component is affixed, or connected, to an intermediate component which in turn is affixed, or connected, to the second component. The joined condition between the first component, and the second component, is intended to remain for the life of the sanitary napkin. Conversely, components are considered "removably affixed" if the components may be detached and separated from each other without destruction or unintended gross deformation of either.

Any joined arrangement that provides for capture of the core intermediate the topsheet and the backsheet and a unitary assembly is suitable. Such an assembly has two mutually opposed major faces, one defined by the topsheet and one defined by the backsheet.

The outwardly oriented (garment facing) face of the backsheet may further comprise means for attaching the sanitary napkin to the undergarment of the wearer. Pressure sensitive adhesive has been commonly found to work well for this purpose. Preferably a strip of longitudinally oriented adhesive provides good protection against either the front or the back of the sanitary napkin becoming detached from the wearer's undergarment. The adhesive strip may be continuous or intermittent. A particularly preferred arrangement utilizes two longitudinally oriented strips, one on each side of the longitudinal centerline.

The backsheet typically extends across the whole of the absorbent structure and can extend into and form part of or all of the sideflaps, side wrapping elements or wings, when present.

Lateral Topsheet 18

The absorbent article of the invention comprises a pair of nonwoven lateral topsheet 18 mainly to improve prevention of side leakage of the fluid.

The lateral topsheets 18 can for example be made of all conventional type of nonwovens, such as carded thermal bonded, spun bonded, hydro entangled, melt blown, and using all range of suitable synthetic or natural fibers such as polypropylene, polyethylene, polyester, rayon, cotton, and in a mixed form or in the form of monocomponent, bicomponent fiber. For example, Pegas a.s (Czech Republic) supplies a suitable nonwoven based of bicomponent fibers made of Polypropylene (PP) as core and Polyethylene (PE) as sheath, with a polymer ratio: PP core 70%/PE sheath 30%.

It may be preferred that the lateral topsheets 18 are made of a material having water-repelling properties, in other words an hydrophobic material, to help preventing side leakage or re-wetting of the body-facing surface of the article. Examples of hydrophobic materials suitable for the lateral topsheet include hydrophobic nonwoven, and the synthetic polymeric materials cited above, in particular polyethylene, polypropylene and their mixtures.

The lateral topsheets 18 may take the form of two parallel stripes extending substantially along the whole length of the longitudinal sides of the absorbent article 10. In such case, typically, the outer side edges of the lateral topsheets are contiguous to the longitudinal sides of the article on its periphery. The inner side edges of the lateral topsheets can be linear or have any other shapes. The lateral topsheets, as shown in FIG. 1, may project outwards in the transverse direction to form side flaps F with parts of the backsheet 14.

Embedded Zone 6

As shown in FIG. 1, the absorbent article of the present invention comprises an embedded zone 6 on each of the lateral topsheet 18 along in the longitudinal direction of the article. The embedded zone 6 is a region extending in a longitudinal direction of the absorbent article, and has a plurality of compressed areas 5, 5a.

As shown in FIG. 2(a), the embedded zone 6 comprises the compressed areas 5, 5a where the lateral topsheet 18 and the topsheet 12 are compressed together so that at least a part of the lateral topsheet is embedded into the topsheet. In one embodiment of the invention, as shown in FIG. 2(b), the embedded zone 6 may include compressed areas where the absorbent core 16 is also at least partially embossed together with the lateral topsheet 18 and the topsheet 12. In the compressed areas 5, 5a, the lateral topsheet embedded into topsheet is single layer. The embedded zones 6 having a plurality of the compressed areas where the lateral topsheets are embedded into the hydrophilic topsheet, the fluid on top of the lateral sheets can be effectively acquired inside the absorbent article as the embedded structure provides more suction of the fluid by the hydrophilic topsheet, and effectively directs the fluid to the inside the absorbent article. In addition, lateral diffusion of the fluid beyond the side edges of the absorbent core is also effectively prevented by the presence of the compressed areas and the lateral topsheets. Prevention of fluid leakage in the absorbent article according to the present invention may be enhanced by employing hydrophobic lateral topsheets.

The embedded zone 6 may be formed to be linear. The width A of the embedded zone 6, as shown in FIG. 1, is the longest distance in the transverse direction between two compressed areas. The width A of the embedded zone 6 may be constant along the longitudinal direction, or may not be. For example, the width A of the embedded zone 6 at one point relatively close to the transverse centerline T may be greater than the width A of the embedded zone 6 at another point relatively close to a front or back end. A width of embedded zone may be in the range of from about 2 mm to about 30 mm, preferable from about 5 mm to about 20 mm. The distance B between embedded zones 6 in the may be in the range of from about 30 mm to about 80 mm, preferable from about 50 mm to about 70 mm.

The embedded zone 6 in the lateral topsheet 18 has a length in the longitudinal direction having a length share of about 50% or more of relative to the length L of the article, and cross a transverse centerline T. In one embodiment, the embedded zones 6 may extend to at least one of a front and a back end edges of the absorbent article. When the embedded zones 6 extend to a front end and back end edges of the absorbent article, it may bond the lateral topsheets 18 and the topsheet 10 without using another bonding means such as glue by providing sufficient bonding strength to the lateral topsheets 18 and the top topsheet 12.

The embedded zone 6 preferably has about 50%, more preferably 60%, of the compressed areas 5, 5a by the total area of the embedded zone 6.

In one embodiment of the present invention, the compressed areas 5, 5a formed in the embedded zone 6 may be arranged substantially continuously in the longitudinal direction. In another embodiment of the present invention, the compressed areas 5, 5a formed in the embedded zone 6 may be arranged substantially continuously in the transversal direction. The term "substantially continuous(ly) in the longitudinal direction", as used herein, defines as follows: Move an imaginary straight line perpendicular to the longitudinal direction in the longitudinal direction in the plan view of the absorbent article. When the line intersects the compressed areas 5, 5a over a length of 80%, preferably 90%, more preferably 100%, of the length G of the embedded zone 6, the compressed areas are considered to be "substantially continuous(ly) in the longitudinal direction." Similarly, the term "substantially continuous(ly) in the transversal direction", as used herein, as follows: Move an imaginary straight line perpendicular to the transversal direction in the transversal direction in the plan view of the absorbent article. When the line intersects the compressed areas 5, 5a over a length of 70%, preferably 90%, more preferably 100%, of the width A of the embedded zone 6, the compressed areas are considered to be "substantially continuous(ly) in the transversal direction."

Hereinafter, "overhang" means, as shown in FIG. 1, the distance E between inner side edge of the lateral topsheet 18 and the compressed area 5a, the compressed area closest to the inner side edge. The overhang is preferably less than about 2 mm, more preferably less than about 1 mm, and more preferably substantially zero.

Outer side edge of the embedded zone 6 may extend in a transverse direction to side edge 610A/610B of the absorbent core 16. Preferably, the outer side edge 600 of the embedded zone 6 may extend outwards from the side edges 610A/610B of the absorbent core 16.

The embedded zones 6 may have at least one of various shapes such as circle, oval, heart shape, triangle, square, rectangle, line, and irregular shapes. The size of each compressed area may have dimension of from about 2 mm to about 10 mm, preferably from about 2 mm to about 5 mm. The distance between the dots may be narrower than about 5 mm, preferable narrow than 2 mm. The dots can be arranged regularly into straight lines or shaped lines or randomly arranged.

The embossing can be achieved with standard techniques such as thermal bond, ultrasonic bond and/or pressure. An example of a suitable process is thermal bonding wherein sheets are passed through two steel rolls where one is engraved with the visual pattern and the other is flat. In certain embodiments, one or both of the rolls are warmed to temperature suitable to at least partially melt one or more sheet or softening one or more sheet layer, typical in the range of from about 60° C. to about 170° C.

The embossing roll may be engraved using conventional techniques such machine tooling for most embossing patterns, but it may be desirable to use acid etching or laser engraving to provide a finer engraving, and thus a finer embossed pattern. It may be desirable that the embossed pattern comprises relatively thin embossing features, much thinner than the embossed channels previously disclosed in the art, such as in WO2004/006818. Thin embossing features may provide a generally feminine and delicate look to the article. The embossing tool should therefore capable of high definition embossing, in particular with a resolution (minimum thickness of the embossed lines) of less than about 0.75 mm, in particular but not limited to between about 0.35 mm and about 0.60 mm. Similarly, the resolution of the printed pattern (corresponding to the minimum thickness of a line) may be of less than about 0.75 mm, in particular but not limited to between about 0.35 mm and about 0.60 mm.

Secondary Topsheet 20

The article of the invention may optionally comprise a secondary topsheet layer intermediate the topsheet 12 and the absorbent core 16.

Such a secondary layer might be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described hereinbefore for the topsheet can be used for the secondary layer. In a preferred embodiment, this secondary topsheet layer underlies the apertured topsheet on the entire surface thereof, i.e., the secondary layer extends to the periphery of the topsheet so that the secondary layer underlies the topsheet on the entire inner surface of the topsheet.

The purpose of the secondary topsheet is normally to readily transfer the acquired body fluid from the topsheet to the absorbent core, the transfer of fluid occurring not only vertically in the thickness of the secondary topsheet, but also along the length and the width directions of the absorbent product. This helps the fluid capacity of the underlying storage layer to be fully utilized. Although preferred, the presence of secondary topsheet is however optional.

Secondary Backsheet

The article of the invention may comprise a secondary backsheet layer intermediate the absorbent core 16 and the backsheet 14. The use of a secondary backsheet is particularly indicated in presence of air permeable backsheet. The purpose of the secondary backsheet is to retard or prevent liquid from passing from the absorbent core to the outside of the product, while allowing free air flow through it. A particularly suitable example of secondary backsheet is a resilient three dimensional polymeric web, which consist of a liquid impervious film which has apertures forming capillarity or cones. The film with capillaries or cones is oriented such us the apex of the cones face the absorbent core, this to prevent passage of fluid. The capillaries or cones can have a slanted shape in order to partly close or completely close when compressed.

Release Paper

The adhesive coated on the backsheet surface are typically provided with a protective cover, which is removed prior to use. The protective cover may be a silicone coated release paper, a plastic film or any other easily removable cover. The protective cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

Method of Manufacture

The absorbent articles of the present invention may comprise the usual layers or components normally found in commercially available standard articles which may be joined together by standard means such as embossing (e.g. thermal bonding) or gluing or combination of both, and the articles may be produced industrially by conventional means. In particular the compressed areas may be applied by conventional heat embossing rolls.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a body-facing surface having a pair of longitudinal side edges, a front region, a back region, a central region extending between the front region and the back region, and a transverse centerline, the absorbent article further comprising;
   a hydrophilic topsheet,
   a backsheet joined to the topsheet,
   an absorbent core disposed between the topsheet and the backsheet, and
   a pair of lateral topsheets, one of the pair of lateral topsheets being on one of the pair of longitudinal side edges, and the other of the pair of lateral topsheets being on the other of the pair of longitudinal side edges of the body-facing surface of the absorbent article so that at least a part of each of the pair of lateral topsheets covers the topsheet where the topsheet covers the absorbent core,
   wherein each of the pair of lateral topsheets comprises an embedded zone along a longitudinal direction of the absorbent article defined by a plurality of compressed areas where the lateral topsheet and the topsheet are jointly compressed so that the lateral topsheet is embedded into the topsheet, wherein each of the embedded zones has a first width which is constant along the longitudinal direction in the central region, and a second width which is constant along the longitudinal direction in both the front region and back region, wherein the first width is greater than the second width, and
   wherein the lateral topsheet in the compressed areas is one layer and wherein said embedded zone has more than about 50% of said compressed areas by the total area of said embedded zone and wherein at least a portion of the compressed areas are disposed inboard of outer side edges of the absorbent core and at least a portion of the compressed areas are disposed outboard of the outer side edges of the absorbent core, and wherein the compressed areas are substantially continuous in the longitudinal direction and substantially continuous in the transversal direction.

2. The absorbent article according to claim 1, wherein each of said lateral topsheets is hydrophobic.

3. The absorbent article according to claim 2, wherein each of said lateral topsheets comprises a hydrophobic nonwoven.

4. The absorbent article according to claim 1, wherein each of said embedded zones has a length in the longitudinal direction having a length of about 50% or more relative to the whole longitudinal length of said absorbent article, and is located to cross the transverse centerline of said absorbent article.

5. The absorbent article according to claim 1, wherein said each of said lateral topsheets has overhang of less than about 2 mm.

6. The absorbent article according to claim 5, wherein said overhang is less than about 1 mm.

7. The absorbent article according to claim 1, wherein the distance between each of the embedded zones is at least about 30 mm.

8. The absorbent article according to claim 7, wherein the distance between each of the embedded zones is at least about 50 mm.

9. The absorbent article according to claim 1, wherein each of said embedded zones has a width in the range of from about 2 mm to about 30 mm-.

10. The absorbent article according to claim 9, wherein each of said embedded zones has a width in the range of from about 5 mm to about 20 mm-.

11. The absorbent article according to claim 1, wherein each of said embedded zones comprises an outer side edge, wherein each of the outer side edges are disposed outboard of the outer side edges of said absorbent core.

12. The absorbent article according to claim 1, wherein each of said embedded zones has more than about 60% of said compressed areas by the total area of said embedded zones.

* * * * *